United States Patent [19]

Robinson

[11] Patent Number: 5,189,229

[45] Date of Patent: Feb. 23, 1993

[54] DEBROMINATING DIBROMOFLUOROMETHANE WITH TRIBUTYLTIN HYDRIDE

[75] Inventor: John M. Robinson, Pinner, England

[73] Assignee: Glaxo Group Limited, London, England

[21] Appl. No.: 591,984

[22] Filed: Oct. 1, 1990

Related U.S. Application Data

[63] Continuation of Ser. No. 316,790, Feb. 28, 1989, abandoned.

[30] Foreign Application Priority Data

Feb. 29, 1988 [GB] United Kingdom ................ 8804693

[51] Int. Cl.$^5$ ...................... C07C 17/00; C07C 19/02
[52] U.S. Cl. ................................................... 570/176
[58] Field of Search ........................................ 570/176

[56] References Cited

U.S. PATENT DOCUMENTS

| | | | |
|---|---|---|---|
| 3,042,727 | 7/1962 | Olstowski et al. | 570/176 |
| 3,082,263 | 3/1963 | McGinty | 570/176 |

FOREIGN PATENT DOCUMENTS

| | | | |
|---|---|---|---|
| 2133152 | 1/1973 | Fed. Rep. of Germany | 570/176 |
| 939920 | 10/1963 | United Kingdom | 570/176 |
| 1249182 | 10/1971 | United Kingdom | 570/176 |

OTHER PUBLICATIONS

Seyferth et al, "J. Org. Chem." (1963) pp. 703–706.

Primary Examiner—Joseph E. Evans
Attorney, Agent, or Firm—Bacon & Thomas

[57] ABSTRACT

Preparation of bromofluoromethane may be effected in good yield by reductive debromination of dibromofluoromethane using an organotin hydride, for example tri-n-butyltin hydride.

13 Claims, No Drawings

DEBROMINATING DIBROMOFLUOROMETHANE WITH TRIBUTYLTIN HYDRIDE

This application is a continuation of application Ser. No. 07/316,790, filed Feb. 28, 1989, now abandoned.

This invention relates to a chemical process and more particularly to a method for the preparation of bromofluoromethane.

Bromofluoromethane is an important reagent in the manufacture of intermediates, pharmaceuticals and other chemicals.

This compound has hitherto been prepared by three basic methods. In one method, bromofluoromethane is prepared from salts of fluoroacetic acid using a Hunsdiecker type of reaction as described by Haszeldine in J. Chem. Soc., 1952, 4259–4268 and U.S. Pat. No. 2716668. In another method, bromofluoromethane is prepared from dibromofluoromethane by reductive debromination with a Swarts reagent as described in the early literature by Swarts et al., Bull. Acad. Roy. Belg. 1910, 113, 23. Other methods prepare bromofluoromethane from a dihalomethane, for example methylene bromide, by an halogen exchange reaction or from a halomethane, for example bromomethane or fluoromethane, by bromination or fluorination over a catalyst such as alumina.

These earlier methods have generally resulted in poor yields or involved the use of dangerous materials.

Seyferth et al. in Journal of Organic Chemistry 1963, 703–706, although presenting no supporting data, describe the incidental preparation of bromofluoromethane by a step-wise reduction of tribromofluoromethane using tri-n-butyltin hydride. However, the reaction conditions described in this paper are such that either no bromofluoromethane will result or the product will contain mixtures of both bromofluoromethane and dibromofluoromethane. Seyferth et al. also use a conventional distillation system under reduced pressure and this we believe will result in low yields of bromofluoromethane since despite obtaining a 69% theoretical yield of dibromofluoromethane from tribromofluoromethane Seyferth et al. failed to obtain appreciable amounts of bromofluoromethane.

Furthermore Seyferth et al. while giving no supporting experimental data specifically for reduction of tribromofluoromethane indicate that 0.02 moles of the hydride reagent were reacted with 0.04 moles of various halomethanes including tribromofluoromethane, at 0° C. for about 1 hour, with stirring at that temperature for 10 minutes and then at room temperature for a further ten minutes. The description of the reaction products is ambiguous in that the yield of dibromofluoromethane is greater than the reactant ratios would suggest. Although it is indicated that some bromofluoromethane was also formed, the above discrepancy throws doubt on the accuracy of this statement. If, however, initially formed dibromofluoromethane was indeed further reduced to bromofluoromethane even when using the above apparently mild conditions there is an implication that it would be difficult if not impossible to use the same technique starting with dibromofluoromethane to displace only a single bromine atom to give useful yields of bromofluoromethane. Seyferth et al. thus do not suggest that organotin hydride reduction of dibromofluoromethane would be a better route to bromofluoromethane than the other methods disclosed above.

We have now found that bromofluoromethane of good quality and purity can be prepared in good yield and more efficiently from dibromofluoromethane by the reductive debromination of substantially pure dibromofluoromethane using an organotin hydride such as tri-n-butyltin hydride.

According to the present invention therefore we provide a process for the production of bromofluoromethane in which substantially pure dibromofluoromethane is subjected to reduction with an organotin hydride.

We have surprisingly found that the tendency, described by Seyferth et al. of certain polyhalomethanes to react too far with such a hydride reagent so as to yield doubly dehalogenated products may be overcome by careful choice of reaction conditions so as to yield a highly pure product. Under the preferred reaction conditions the dibromofluoromethane may be reacted with at least a substantially equal molar quantity of the hydride reagent so as to ensure substantially complete reaction and minimise contamination with unreacted starting material. The term "a substantially equal molar quantity" is intended to cover ratios of organotin hydride to dibromofluoromethane between 0.8:1 and 1.5:1, more preferably 0.9:1 to 1.3:1.

The good yield and purity of the reaction may be enhanced by use of a reflux condenser, e.g. a cold finger or water condenser, during the reduction to return unreacted dibromofluoromethane to the reaction vessel; where a water condenser is used this may be connected to one or more cold traps capable of condensing bromofluoromethane, e.g. a cold finger at −196° to −40° C. This system will permit some vapourised bromofluoromethane to distill over during the reduction, thereby removing it from the reaction system. However, we have found that bromofluoromethane which vapourises during the reduction carries with it even at 0° C. to 5° C., some dibromofluoromethane reactant. Consequently, where a water condenser is used in this way a further cold finger trap, e.g. at −35° C. to +10° C., is desirably provided before the −196° to −40° C. trap to condense and remove any vapourised dibromofluoromethane.

However, instead of allowing bromofluoromethane to distill during the reduction, it may be preferable to use a reflux condenser such as a cold finger, at much lower temperatures, e.g. −196° to −40° C., to return both dibromofluoromethane and bromofluoromethane to the reaction, and to begin distillation only when reduction is completed. In this case, the reflux cold finger will clearly have to be removed prior to distillation.

Distillation is preferably effected at substantially atmospheric pressure at relatively low temperatures, for example 0° to 100° C., preferably 20°–45° C. Such distillation is slow, for example taking place over a period of 0.5 to 15 hours, preferably 2–12 hours, for example 2–6 hours.

A steady flow of an inert gas such as nitrogen purging through the reaction mixture during distillation is particularly advantageous to increase the rate of collection of bromofluoromethane. During distillation a series of cold finger traps are advantageously provided whereby unreacted dibromofluoromethane is collected in a first trap for example at −35° to +10° C., e.g. an ice/salt trap, and the desired bromofluoromethane in a second trap or traps at much lower temperatures, e.g. at −196° to −40° C.

Cold finger traps which can be used are dry ice (solid carbon dioxide)/acetone (ca. −78° C.), dry ice/carbon tetrachloride (ca. −20° C.), dry ice/methanol (ca. −70° C.) or liquid nitrogen (ca. −196° C.). Dry ice/acetone (ca. −78° C.) is preferred.

Thus, in general dibromofluoromethane may be contacted with the tri-n-butyltin hydride at a temperature in the range of −20° C. to +30° C., preferably −5° C. to +10° C. The tri-n-butyl tin hydride is preferably added slowly, e.g. over a period of 0.5 to 10 hours. The reaction vessel is advantageously fitted with either a water condenser (5° C. to 50° C.) or a cold finger (−196° C. to 5° C.) as explained above.

The reaction of the dibromofluoromethane with the tri-n-butyltin hydride is exothermic and cooling is usually necessary to maintain the reaction temperature at temperatures in the preferred range −5° C. to +10° C. We have found that the presence of a free radical initiator such as α, α'-azoisobutyronitrile in the reaction and/or additional illumination, for example from a tungsten bulb, moderates the exothermic effect. Such a free radical initiator may, for example, be included in the reaction mixture at a level of up to 5% by weight relative to the dibromofluoromethane, preferably 0.1-1% by weight.

After addition of the tri-n-butyl tin hydride, the mixture is advantageously further stirred at −20° C. to +30° C., preferably −5° C. to +10° C., for 0.1 to 10 hours to ensure completion of the reaction.

For distillation, the reflux cold finger if used is removed and the mixture is warmed to between 0° C. and 100° C. and stirred for a further 0.5 to 15 hours with a steady flow of nitrogen purging through the reaction flask and trap(s), advantageously at a rate of 5-500 ml per minute. During the distillation period bromofluoromethane may be collected in a cold finger trap at −40° C. to −196° C. An additional cold finger trap at −35° C. to +10° C. can be inserted between the reaction flask and the −40° C. to −196° C. trap to reduce the amount of dibromofluoromethane condensing in the second trap.

The invention is illustrated by the following examples. Dibromofluoromethane was obtained from Fluorochem Ltd., of Old Glossop, Derbyshire, England and tri-n-butyltin hydride from Aldrich, Gillingham, Dorset, England.

EXAMPLE 1

Preparation of bromofluoromethane from dibromofluoromethane using tri-n-butyltin hydride Tri-n-butyltin hydride (25 g) was added from a dropping funnel over 2 hours to cold (5° C.) dibromofluoromethane (16.5 g) contained in a flask fitted with a nitrogen inlet and a cold water reflux condenser to return vapourised dibromofluoromethane to the reaction. The reaction mixture was warmed to between 25° C. and 30° C. and with a steady flow of nitrogen purging through the reaction flask and traps the reaction mixture was stirred for a further 2.5 hours. During the addition and warming up periods bromofluoromethane (8.7 g) was taken off from the reflux condenser and collected in a dry ice/acetone cold finger trap (ca. −78° C.). An ice/salt cold finger trap (−10° C.) was present between the reaction flask and the −78° C. trap to reduce the amount of dibromofluoromethane condensing in the second trap. The product was identified by its boiling point (17° C.) and n.m.r. spectrum (10% v/v CDCl$_3$, delta=6.1, doublet). G.l.c. showed 11% impurities (8% dibromofluoromethane) giving a corrected theoretical yield of 79.8%.

EXAMPLE 2

Preparation of bromofluoromethane from dibromofluoromethane using tri-n-butyltin hydride Tri-n-butyltin hydride (181.8 g, 1.2 equivalents) was added from a dropping funnel over 1 hour to cold (5° C.) dibromofluoromethane (100 g) in a reaction flask fitted with a nitrogen inlet and a dry ice/acetone cold finger reflux condenser (ca. −78° C.) to return vapourised bromofluoromethane and dibromofluoromethane to the reaction, the condenser leading to a dry ice/acetone cold finger trap (−78° C.) for eventual collection of bromofluoromethane. The temperature was maintained between 0° C. and 5° C. during the addition. The mixture was further stirred for 1 hour at 0° C. to 5° C. The dry ice/acetone cold finger reflux condenser was removed, the mixture warmed to 40° C. and with a steady flow of nitrogen purging through the reaction flask and traps, the reaction mixture was stirred for a further 5 hours. During the warming up and stirring periods bromofluoromethane (51 g) was collected in the dry ice/acetone cold finger trap. The product was identified by its boiling point (17° C.) and n.m.r. spectrum (10% v/v CDCl$_3$, delta=6.1, doublet). G.l.c. showed 5.7% impurities (0.8% dibromofluoromethane) giving a corrected theoretical yield of 81.8%.

EXAMPLE 3

Preparation of bromofluoromethane from dibromofluoromethane using tri-n-butyltin hydride Tri-n-butyltin hydride (1.89 kg, 1.2 equivalents) was added from a dropping funnel over 1 hour 15 min to cold (5° C.) dibromofluoromethane (1.04 Kg) in a reaction flask fitted with a nitrogen inlet and a dry ice/acetone cold finger reflux condenser (ca −78° C.) to return vapourised bromofluoromethane and dibromofluoromethane to the reaction, the condenser leading to a dry ice/acetone cold finger trap (−78° C.) for eventual collection of bromofluoromethane. The temperature was maintained between 0° C. and 5° C. during the addition. The mixture was further stirred for 1 hour at 0° C. to 5° C. The dry ice/acetone cold finger reflux condenser was removed, the mixture warmed to 40° C. and with a steady flow of nitrogen purging through the reaction flask and traps, the reaction mixture was stirred for a further 3 hours. The reaction mixture was then warmed to 70° C. and then stirred for a further 9 hours. During the warming up and stirring periods bromofluoromethane (510 g) was collected in the dry ice/acetone cold finger trap. The product was identified by its boiling point (17° C.) and nmr spectrum (10% v/v CDCl$_3$, delta=6.1, doublet). Glc showed 4.7% impurities (0.2% dibromofluoromethane) giving a corrected theoretical yield of 79.3%.

EXAMPLE 4

Preparation of bromofluoromethane from dibromofluoromethane using tri-n-butyltin hydride Tri-n-butyltin hydride (1.89 kg, 1.2 equivalents) was added from a dropping funnel over 1 hour 15 min to cold (5° C.) dibromofluoromethane (1.04 kg) and α, α'-azoisobutyronitrile (AIBN) (1.04 g) in a reaction flask fitted with a nitrogen inlet and a dry ice/acetone cold finger reflux condenser (ca −78° C.) to return vapourised bromofluoromethane and dibromofluoromethane to the reaction, the condenser leading to a dry ice/acetone cold finger trap (−78° C.) for eventual collection of bromofluoromethane. The temperature was maintained between 0° C. and 5° C. during the addition. The mixture was further stirred for 1 hour at 0° C. to 5° C. The dry ice/acetone cold finger reflux condenser was removed, the mixture warmed to 40° C. and with a steady flow of nitrogen purging through the reaction flask and traps, the reaction mixture was stirred for a further 3 hours. The reaction mixture was then warmed to 70° C. and then stirred for a further 9 hours. During the warming up and stirring periods bromofluoromethane (470 g) was collected in the dry ice/acetone cold finger trap. The product was identified by its boiling point (17° C.) and nmr spectrum (10% v/v $CDCl_3$, delta=6.1, doublet). Glc showed 3.9% impurities (0.7% dibromofluoromethane) giving a corrected theoretical yield of 72.1%.

I claim:

1. A process for the production of bromofluoromethane in which substantially pure dibromofluoromethane is subjected to reduction with an organotin hydride wherein the ratio of organotin hydride to dibromofluoromethane is 0.9:1 to 1.3:1, and wherein the reaction is carried out with condensing means serving to condense and return any evaporating dibromofluoromethane to the reaction mixture during the continuance of the reaction.

2. A process as claimed in claim 1 in which the organotin hydride is a tri-n-butyltin hydride.

3. A process as claimed in claim 1 in which the reaction temperature is maintained in the range −20° C. to +30° C.

4. A process as claimed in claim 1 in which the reaction is effected in the presence of a free radical initiator.

5. A process as claimed in claim 4 wherein the free radical initiator is $\alpha, \alpha'$-azoisobutyronitrile.

6. A process as claimed in claim 4 or 5 wherein the free radical initiator is included in the reaction mixture at a level of up to 5% by weight relative to the dibromofluoromethane.

7. A process as claimed in claim 6 wherein the free radical initiator is included at a level of from 0.1 to 1% by weight relative to the dibromofluoromethane.

8. A process as claimed in claim 1 wherein the reaction is effected in the presence of additional illumination.

9. A process as claimed in claim 1 in which the reaction is carried out in a vessel fitted with a reflux condenser serving to condense and return any evaporating dibromofluoromethane to the reaction mixture during the continuance of the reaction.

10. A process as claimed in claim 9 in which the reflux condenser also serves to condense and return any evaporating bromofluoromethane.

11. A process as claimed in claim 1 in which bromofluoromethane and unreacted dibromofluoromethane are distilled from the reaction mixture and prior to condensation and collection of bromofluoromethane unreacted dibromofluoromethane is removed by condensation at a temperature in the range −35° C. to +10° C.

12. A process as claimed in claim 1 in which distillation is initiated after completion of the reaction.

13. A process as claimed in claim 12 in which an inert gas is caused to flow through the reaction mixture to enhance the rate of collection of bromofluoromethane.

* * * * *